(12) United States Patent
Hull et al.

(10) Patent No.: US 10,520,407 B2
(45) Date of Patent: Dec. 31, 2019

(54) NANO-INDENTATION TESTS TO CHARACTERIZE HYDRAULIC FRACTURES

(71) Applicant: Saudi Arabian Oil Company, Dhahran (SA)

(72) Inventors: Katherine Leigh Hull, Houston, TX (US); Younane N. Abousleiman, Norman, OK (US)

(73) Assignee: Saudi Arabian Oil Company, Dhahran (SA)

(*) Notice: Subject to any disclaimer, the term of this patent is extended or adjusted under 35 U.S.C. 154(b) by 117 days.

(21) Appl. No.: 15/909,659

(22) Filed: Mar. 1, 2018

(65) Prior Publication Data
US 2019/0271622 A1    Sep. 5, 2019

(51) Int. Cl.
G01N 3/42    (2006.01)
G01N 3/06    (2006.01)

(52) U.S. Cl.
CPC .............. *G01N 3/42* (2013.01); *G01N 3/066* (2013.01); *G01N 2203/0067* (2013.01)

(58) Field of Classification Search
CPC ... G01N 3/42; G01N 3/066; G01N 2203/0067
USPC ........................................................ 73/821
See application file for complete search history.

(56) References Cited

U.S. PATENT DOCUMENTS

| 830,437 | A | 9/1906 | Humphrey |
| 3,284,281 | A | 11/1966 | Thomas |
| 3,807,557 | A | 4/1974 | Miller |
| 3,926,575 | A | 12/1975 | Meyers |
| 4,043,885 | A | 8/1977 | Yen et al. |
| 4,220,550 | A | 9/1980 | Frenier et al. |

(Continued)

FOREIGN PATENT DOCUMENTS

| CN | 105445440 | 3/2016 |
| WO | 2004/005435 | 1/2004 |

(Continued)

OTHER PUBLICATIONS

"Field-Deployable Solution for Nanoporosity Measurements in Mud Logging Operations and a Novel Method for Fracability Analysis Using Mud Cuttings," Agilent Technologies, Oct. 2013, 44 pages.

(Continued)

*Primary Examiner* — Octavia Hollington
(74) *Attorney, Agent, or Firm* — Fish & Richardson P.C.

(57) ABSTRACT

A rock sample is nano-indented from a surface of the rock sample to a specified depth less than a thickness of the rock sample. While nano-indenting, multiple depths from the surface to the specified depth and multiple loads applied to the sample are measured. From the multiple loads and the multiple depths, a change in load over a specified depth is determined, using which an energy associated with nano-indenting rock sample is determined. From a Scanning Electron Microscope (SEM) image of the nano-indented rock sample, an indentation volume is determined responsive to nano-indenting, and, using the volume, an energy density is determined. It is determined that the energy density associated with the rock sample is substantially equal to energy density of a portion of a subterranean zone in a hydrocarbon reservoir. In response, the physical properties of the rock sample are assigned to the portion of the subterranean zone.

15 Claims, 5 Drawing Sheets

(56) References Cited

U.S. PATENT DOCUMENTS

| | | | |
|---|---|---|---|
| 4,289,639 A | 9/1981 | Buske | |
| 4,324,560 A | 4/1982 | Fonseca | |
| 4,381,950 A | 5/1983 | Lawson | |
| 4,594,170 A | 6/1986 | Brown et al. | |
| 4,640,692 A | 2/1987 | Audeh | |
| 5,302,297 A | 4/1994 | Barthrope | |
| 5,999,887 A | 12/1999 | Giannakopoulos et al. | |
| 6,138,760 A | 10/2000 | Lopez et al. | |
| 6,749,022 B1 | 6/2004 | Fredd | |
| 6,866,048 B2 | 3/2005 | Mattox | |
| 6,947,843 B2 | 9/2005 | Fisher et al. | |
| 7,098,663 B1 | 8/2006 | Bader | |
| 7,565,831 B2 | 7/2009 | Miyahara | |
| 8,380,437 B2 | 2/2013 | Abousleiman et al. | |
| 8,701,788 B2 | 4/2014 | Wigand et al. | |
| 8,839,860 B2 | 9/2014 | Wigand et al. | |
| 8,851,177 B2 | 10/2014 | Wigand | |
| 8,936,089 B2 | 1/2015 | Wigand | |
| 10,151,715 B2 * | 12/2018 | Hull | G01V 5/00 |
| 10,351,758 B2 * | 7/2019 | Hull | C09K 8/58 |
| 10,379,068 B2 * | 8/2019 | Hull | G01N 23/20025 |
| 2007/0298979 A1 | 12/2007 | Perry et al. | |
| 2008/0006410 A1 | 1/2008 | Looney et al. | |
| 2008/0070806 A1 | 3/2008 | Lin et al. | |
| 2009/0193881 A1 | 8/2009 | Finnberg | |
| 2010/0010106 A1 | 1/2010 | Crews | |
| 2010/0186520 A1 | 7/2010 | Wheeler | |
| 2010/0213579 A1 | 8/2010 | Henry | |
| 2010/0279136 A1 | 11/2010 | Bonucci | |
| 2012/0247774 A1 | 10/2012 | Li et al. | |
| 2013/0160994 A1 | 6/2013 | Alsop et al. | |
| 2013/0269933 A1 | 10/2013 | Pomerantz et al. | |
| 2014/0008305 A1 | 1/2014 | Nichols et al. | |
| 2014/0048694 A1 | 2/2014 | Pomerantz | |
| 2014/0116710 A1 | 5/2014 | Naser-El-Din et al. | |
| 2014/0374104 A1 | 12/2014 | Kushal | |
| 2015/0293256 A1 | 10/2015 | Dusterhoft | |
| 2017/0066959 A1 | 3/2017 | Hull et al. | |
| 2017/0067836 A1 | 3/2017 | Hull et al. | |

FOREIGN PATENT DOCUMENTS

| | | |
|---|---|---|
| WO | 2012/087887 | 6/2012 |
| WO | 2013/149122 | 10/2013 |
| WO | 2017/040834 | 3/2017 |
| WO | 2017/086975 | 5/2017 |

OTHER PUBLICATIONS

Abad et al., "Evaluation of the Material Properties of the Multilayered Oxides formed on HCM12A using New and Novel Techniques," Manuscript Draft, Manuscript No. OXID-D-15-00019, published in 2015, 44 pages.

Abousleiman et al, "A Micromechanically Consistent Poroviscoelasticity Theory for Rock Mechanics Applications," Int. J. Rock Mech. Min. Sci. & Geomech. Abstr., vol. 30, No. 7, published in 1993, 4 pages.

Abousleiman et al, "Anisotropic Porothermoelastic Solution and Hydro-Thermal Effects on Fracture Width in Hydraulic Fracturing," Int. J. Numer. Anal. Meth. Geomech., published in 2013, 25 pages.

Abousleiman et al, "Poroviscoelastic Analysis of Borehole and Cylinder Problems," ACTA Mechanica, vol. 119, published in 1996, 21 pages.

Abousleiman et al, "SPE 110120: Geomechanics Field and Laboratory Characterization of Woodford Shale: The Next Gas Play," SPE International, SPE 110120, presented at the 2007 SPE Annual Technical Conference and Exhibition on Nov. 11-14, 2007, 14 pages.

Abousleiman et al., "GeoGenome Industry Consortium (G2IC)," JIP, 2004-2006, 6 pages.

Abousleiman et al., "Geomechanics Field Characterization of the Two Prolific U.S. Mid-West Gas Plays with Advanced Wire-Line Logging Tools," SPE International, SPE 124428, presented at 2009 SPE Annual Technical Conference and Exhibition, Oct. 4-7, 2009, 19 pages.

Abousleiman et al., "Geomechanics field characterization of Woodford Shale and Barnett Shale with advanced logging tools and nano-indentation on drill cuttings," The Leading Edge, Jun. 2010, 6 pages.

Abousleiman et al., "Mandel's Problem Revisited," Geotechnique, 46, No. 2, published in 1996, 9 pages.

Abousleiman et al., "Mechanical Characterization of Small Shale Samples subjected to Fluid Exposure using the Inclined Direct Shear Testing Device," Int. J. Rock Mech. & Min. Sci., vol. 47, No. 3, published in 2010, 13 pages.

Abousleiman et al., "Poroelastic Solutions in Transversely Isotropic Media for Wellbore and Cylinder," Int. J. Solids Structures, vol. 35, Nos. 34-35, published in 1998, 25 pages.

Abousleiman et al., "The Granular and Polymer Composite Nature of Kerogen-Rich Shale," Acta Geotechnica, Feb. 5, 2016, 24 pages.

Allan et al., "A Multiscale Methodology for the Analysis of Velocity Anisotropy in Organic-Rich Shale," Geophysics, vol. 80, No. 4, Jul.-Aug. 2015, 16 pages.

Ananthan et al., "Influence of Strain Softening on the Fracture of Plain Concrete Beams," Int. J. of Fracture, vol. 45, published in 1990, 25 pages.

Ballice, "Solvent Swelling Studies of Goynuk (Kerogen Type-I) and Beypazari Oil Shales (Kerogen Type-II)," Science Direct, Fuel vol. 82, published in 2003, 5 pages.

Bazant et al., "Deformation of Progressively Cracking Reinforced Concrete Beams," ACI Journal, Technical Paper, Title No. 81-26, vol. 81, No. 3, May-Jun. 1984, 11 pages.

Bazant et al., "Strain-Softening Bar and Beam: Exact Non-Local Solution," Int. J. Solids Structures, vol. 24, No. 7, published in 1988, 15 pages.

Bennett et al., "Instrumented Nanoindentation and 3D Mechanistic Modeling of a Shale at Multiple Scales," Acta Geotechnica, vol. 10, No. 21, Jan. 9, 2015; 14 pages.

Bhandari et al., "Two-Dimensional DEM Analysis of Behavior of Geogrid-Reinforced Uniform Granular Bases under a Vertical Cyclic Load, Acta Geotechnica," published in 2014, 12 pages.

Biot, "General Theory of Three-Dimensional Consolidation," Journal of Applied Physics, vol. 12, No. 2, Feb. 1941, 11 pages.

Bobko et al., "The Nanogranular Origin of Friction and Cohesion in Shale—A Strength Homogenization Approach to Interpretation of Nanoindentation Results," Int. J. Numer. Anal. Meth. Geomech., published in 2010, 23 pages.

Boskey et al., "Perspective—Collagen and Bone Strength," Journal of Bone and Mineral Research, vol. 14, No. 3, published in 1999, 6 pages.

Chen et al., "Size Effect in Micro-Scale Cantilever Beam Bending,"Acta Mech., published in 2011, 17 pages.

Chern et al., "Deformation of Progressively Cracking Partially Prestressed Concrete Beams," PCI Journal, vol. 37, No. 1, published in 1992, 11 pages.

Chupin et al., "Finite Strain Analysis of Nonuniform Deformation Inside Shear Bands in Sands," Int. J. Numer. Anal. Meth. Geomech., published in 2012, 16 pages.

Corapcioglu, "Fracturing Fluid Effects on Young's Modulus and Embedment in the Niobrara Formation," Thesis for degree of Master of Science (Petroleum Engineering), Colorado School of Mines, 2014, 189 pages.

Daneshy, Ali; :Hydraulic Fracturing to Improve Production; Tech 101, TheWayAhead, vol. 6, No. 3, 2010; 4 pages.

De Block et al., "SPE-177601-MS: A New Solution for the Characterization of Unconventional Shale Resources Based on Analysis or Drill Cutting," SPE International, presented at the Abu Dhabi International Petroleum Exhibition and Conference, Nov. 9-12, 2015, 6 pages.

Deirieh et al., "Nanochemomechanical Assessment of Shale: A Coupled WDS-Indentation Analysis," Acta Geotechnica, published in 2012, 25 pages.

(56) References Cited

OTHER PUBLICATIONS

Delafargue and Ulm, "Explicit approximations of the indentation modulus of elastically orthotropic solids for conical indenters," International Journal of Solids and Structures vol. 41, Issue 26, Dec. 2004, 10 pages.
Ekbote et al., "Porochemoelastic Solution for an Inclied Borehole in a Transversely Isotropic Formation," J. of Eng. Mech., ASCE, Jul. 2006, 10 pages.
Elijah, "Numerical Modeling of Wellbore Instability (Tensile Failure) Using Fracture Mechanics Approach," Thesis for the degree of Master of Science, African University of Science and Technology Abuja, May 2013, 77 pages.
Ertas et al., "Petroleum Expulsion Part 1. Theory of Kerogen Swelling in Multicomponent Solvents," Energy & Fuels, published in 2006, 6 pages.
Ewy, "Shale Swelling/Shrinkage and Water Content Change due to Imposed Suction and Due to Direct Brine Contact," Acta Geotechnica, published in 2014, 18 pages.
Frazer et al., "Localized Mechanical Property Assessment of SiC/SiC Composite Materials," Science Direct, Part A 70, published in 2015, 9 pages.
Gao et al., "Materials Become Insensitive to Flaws at Nanoscale: Lessons from Nature," PNAS, vol. 100, No. 10, May 13, 2003, 628 pages.
Garnero, "The Contribution of Collagen Crosslinks to Bone Strength," Int. Bone & Mineral Society, Sep. 2012, 8 pages.
Georgi et al., "Physics and Chemistry in Nanoscale Rocks", Mar. 22-26, 2015, La Jolla, California, USA, SPE Forum Series; 4 pages.
Glossary.oilfield.slb.com' [online], "Oilfield Glossary: fluid-friction reducer," available on or before Jun. 15, 2017, retrieved from URL< http://www.glossary.oilfield.slb.com/Terms/f/fluid-friction_reducer. aspx>, 1 page.
Glover et al., "ARMA 16-0737: The Use of Measurements Made on Drill Cuttings to Construct and Apply Geomechanical Well Profiles," ARMA, presentation at the 50th US Rock Mechanics/Geomechanics Symposium, Jun. 26-29, 2016, 11 pages.
Goodman, "Introduction to Rock Mechanics," John Wiley & Sons, Chapter 3: Rock Strength and Failure Criteria; 21 pages.
Han et al., "LBM-DEM Modeling of Fluid-Solid Interaction in Porous Media," Int. J. Numer. Anal. Meth. Geomech., published in 2013, 17 pages.
Hoang et al., "Correspondence Principle Between Anisotropic Poroviscoelasticity and Poroelasticity using Micromechanics and Application to Compression of Orthotropic Rectangular Strips," Journal of Applied Physics, American Institute of Physics, vol. 112, Aug. 30, 2012; 16 pages.
Hornby et al., "Anisotropic Effective-Medium Modeling of the Elastic Properties of Shales," Geophysics, vol. 59, No. 10, Oct. 1994, 14 pages.
Hosemann et al, "Mechanical Characteristics of SiC Coating Layer in TRISO Fuel Particles," Journal of Nuclear Materials, vol. 442, published in 2013, 10 pages.
Hosemann et al., "An Exploratory Study to Determine Applicability of Nano-Hardness and Micro-compression Measurments for Yield Stress Estimation," Science Direct, published in 2008, 9 pages.
Hydraulic Fracturing Fluid Product Component Information Disclosure; 2 pages.
Iqbal et al., "In situ micro-cantilver tests to study fracture properties of NiAl single crystals," Acta Materialia, vol. 60, No. 3, Feb. 2012; 8 pages.
Iyengar et al., "Analysis of Crack Propagation in Strain-Softening Beams," Engineering Fracture Mechanics, published in 2002, 18 pages.
Jia et al., "Highly Efficient Extraction of Sulfate Ions with a Tripodal Hexaurea Receptor," Angew. Chem. Int. Ed., published in 2011, vol. 50, pp. 486-490.
Jose et al., "Continuous multi cycle nanoindentation studies on compositionally graded $Ti_{1-x}Al_xN$ multilayer thin films," (XP028230250) Materials Science and Engineering: A, Elsevier, vol. 528, No. 21, Apr. 20, 2011; 7 pages.

Kelemen et al., "Petroleum Expulsion Part 2. Organic Matter Type and Maturity Effects on Kerogen Swelling by Solvents and Thermodynamic Parameters for Kerogen from Regular Solution Theory," Energy & Fuels, published in 2006, 8 pages.
Kolymbas, "Kinematics of Shear Bands," Acta Geotechnica, published in 2009, 4 pages.
Kumar et al., "SPE 159804: Nano to Macro Mechanical Characterization of Shale," SPE International, presented at the SPE Annual Technical Conference and Exhibition, Oct. 8-10, 2012, 23 pages.
Lam et al., "Experiments and Theory in Strain Gradient Elasticity," J. Mech. and Phys. of Solids, published in 2003, 32 pages.
Larsen et al., "Changes in the Cross-Link Density of Paris Basin Toarcian Kerogen During Maturation," Organic Geochemistry, published in 2002, 10 pages.
Laurent Brochard et al.; "Fracture Properties of Kerogen and Importance for Organic-Rich Shales"; Annual World Conference on Carbon (Carbon 2013), Jul. 2013, Rio de Janeiro, Brazil. HAL ID: hal-01274161, 6 pages.
Li et al., "Mechanical Characterization of Micro/Nanoscale Structures for MEMS/NEMS Applications using Nanoindentation Techniques," Science Direct, published in 2003, 775 pages.
Liu, "Dimension effect on mechanical behavior of silicon micro—cantilver beams," Measurement, vol. 41, No. 8, Oct. 2008; 11 pages.
Liu, "Fracture Toughness Assessment of Shales by Nanoindentation," Thesis for the degree of Master of Science in Civil Engineering, Geotechnical Engineering Masters Projects, University of Massachusetts Amherst, Sep. 2015, 80 pages.
Liu, "Micro—cantilver Testing to Evaluate the Mechanical Properties of Thermal Barrier Coatings," 19th European Conference on Fracture (ECF19): Fracture Mechanics for Durability, Reliability and Safety; Conference Proceedings held Aug. 26-31, 2012, Kazan, Russia; 7 pages.
Mahabadi et al., "A novel approach for micro-scale characterization and modeling of geomaterials incorporating actual material heterogeneity," (XP002689941) Geophysical Research Letters, American Geophysical Union, vol. 39, No. 1, L01303, Jan. 1, 2012; 6 pages.
Mahmoud et al., "Removal of Pyrite and Different Types of Iron Sulfide Scales in Oil and Gas Wells without H2S Generation," (IPTC-18279-MS) Presented at the International Petroleum Technology Conference (IPTC), Doha, Qatar, Dec. 6-9, 2015; 8 pages.
Maio et al., "Measuring Fracture Toughness of Coatings using Focused-ion-beam-machined Microbeams," published in 2004, 4 pages.
Maxwell, "Microseismic hydraulic fracture imaging: The path toward optimizing shale gas production," The Leading Edge, Mar. 2011, 6 pages.
Mesa, "Spherical and rounded cone nano indenters," Micro Star Technologies Inc., available on or before Jan. 23, 2018, 24 pages.
Montgomery, Carl "Fracturing Fluid Components", Chapter 2, Intech open science | open minds, Montgomery ; licensee Intch. 2013, 21 pages; http://dx.doi.oorg/10.5772/56422.
Moyer, "A Case for Molecular Recognition in Nuclear Separations: Sulfate Separation from Nuclear Wastes," Inorganic Chemistry, copyright 2012, pp. 3473-3490.
Oliver and Pharr, "An improved technique for determining hardness and elastic modulus using load and displacement sensing indentation experiments," Journal of Materials Research, vol. 7, No. 6, Jun. 1992, 20 pages.
Oliver and Pharr, "Measurement of hardness and elastic modulus by instrumented indentation: Advances in understanding and refinements to methodology," Journal of Materials Research, vol. 19, No. 1, Jan. 2004, 18 pages.
Oliver, "An Improved Technique for Determining Hardness and Elastic Modulus using Load and Displacement Sensing Indentation Experiments," published in 1992, 20 pages.
Ortega et al., "The Effect of Particle Shape and Grain-Scale Properties of Shale: A Micromechanics Approach," Int. J. Numer. Anal. Methd. Geomech., published in 2010, 33 pages.
Ortega et al., "The Effect of the Nanogranular Nature of Shale on their Poroelastic Behavior," Acta Geotechnica, published in 2007, 28 pages.
Ortega et al., "The Nanogranular Acoustic Signature of Shale," Geophysics, vol. 74, No. 3, May-Jun. 2009, 20 pages.

(56) References Cited

OTHER PUBLICATIONS

Pant, "Nanoindentation characterization of clay minerals and clay-based hybrid bio-geomaterials," disseration for degree of Doctor of Philosophy in the Department of Civil and Environmental Engineering at the Louisiana State University and Agricultural and Medical College, Dec. 2013, 111 pages.
Passey et al., "From Oil-Prone Source Rock to Gas-Producing Shale Reservoir—Geologic and Petrophysical Characterization of Unconventional Shale-Gas Reservoirs," Society of Petroleum Engineers International, CPS/SPE International Oil & Gas Conference and Exhibition, Beijing, China, Jun. 8-10, 2010, 29 pages.
Podio et al., "Dynamic Properties of Dry and Water-Saturated Green River Shale under Stress," Jun. 11, 1968, SPE 1825, 16 pages.
Poon et al., "An Analysis of Nanoindentation in Linearly Elastic Solids," International Journal of Solids and Structures, vol. 45, No. 24, Dec. 1, 2008; 16 pages.
Rajbanshi et al., "Sulfate Separation from Aqeous Alkaline Solutions by Selective Crystallization of Alkali Metal Coordination Capsules," Cryst. Growth Des., published in 2011, pp. 2702-2706.
Richard et al, "Slow Relaxation and Compaction of Granular Systems," Nature Materials, vol. 4, Feb. 2005, 8 pages.
Shin et al., "Development and Testing of Microcompression for Post Irradiation Characterization of ODS Steels," J. Nuclear Materials, published in 2014, 6 pages.
Shukla et al., "ARMA 13-578: Nanoindentation Studies on Shales," ARMA, presented at the 47th US Rock Mechanics/Geomechanics Symposium, Jun. 23-26, 2013, 10 pages.
Sierra et al., "Woodford Shale Mechanical Properties and the Impacts of Lithofacies," ARMA 10-461, copyright 2010, 10 pages.
Singh et al., "Facies classification based on seismic waveform," presented at the 5th Conference & Exposition on Petroleum Geophysics, Jan. 15-17, 2004, 7 pages.
Siskin et al., "Reactivity of organic compounds in hot water: geochemical and technological implications," Science, Oct. 11, 1991, 8 pages.
Slatt et al., "Merging Sequence Stratigraphy and Geomechanics for Unconventional Gas Shales," The Leading Edge, Mar. 2011, 8 pages.
Slatt et al., "Outcrop/Behind Outcrop (Quarry), Multiscale Characterization of the Woodford Gas Shale," copyright 2011, 22 pages.
Sone et al., "Mechanical Properties of Shale-Gas Reservoir Rocks—Part 1: Static and Dynamic Elastic Properties and Anisotropy," Geophysics, vol. 78, No. 5, Sep.-Oct. 2013, 12 pages.
Sone et al., "Mechanical properties of shale-gas reservoir rocks—Part 2: Ductile creep, brittle strength, and their relation to the elastic modulus," 2013, Geophysics, vol. 78, No. 5, 10 pages.
Ulm et al., "Material Invariant Poromechanics Properties of Shales," published in 2005, 8 pages.
Ulm et al., "The Nanogranular Nature of Shale," Acta Geotechnica, published in 2006, 12 pages.
Vanlandingham, "Review of Instrumented Indentation," Journal of Research of the National Institute of Standards and Technology, vol. 108, No. 4, Jul.-Aug. 2003; 17 pages.
Vernik et al., "Ultrasonic Velocity and Anisotropy of Hydrocarbon Source Rocks," Geophysics, vol. 57, No. 5, May 1992, 9 pages.
Wang et al., "A Numerical Study of Factors Affecting the Characterization of Nanoindent ation on Silicon," Materials Science and Engineering: A, vol. 447, No. 1, Feb. 25, 2007; 10 pages.
Wang et al., "Iron Sulfide Scale Dissolvers: How Effective Are They?" Presented at the SPE Saudi Arabia section Annual Technical Symposium and Exhibition (SPE-168063-MS), Khobar, Saudi Arabia, May 19-22, 2013; 22 pages.
Warpinski, "Understanding Hydraulic Fracture Growth, Effectiveness, and Safety Through Microseismic Monitoring," Intech, May 17, 2013, 14 pages.
Wenk et al., "Preferred Orientation and Elastic Anisotropy of Illite-Rich Shale," Geophysics, vol. 72, No. 2, Mar.-Apr. 2007, 7 pages.
Wessels et al., "Identifying fault activation during hydraulic stimulation in the Barnett shale: source mechanisms, b values, and energy release analyses of microseismicity," presented at the SEG San Antonio 2011 Annual Meeting, Sep. 18-23, 2011, 5 pages.
Wilson et al., "Fracture testing of bulk silicon microcantilever beams subjected to a side load," Journal of Microelectromechanical Systems, vol. 5, No. 3, Sep. 1996; 9 pages.
Wurster et al., "Characterization of the fracture toughness of microsized tungsten single crystal notched specimens," Philosophical Magazine, vol. 92, No. 14, May 2012; 23 pages.
Zeszotarski et al., "Imaging and Mechanical Property Measurements of Kerogen via Nanoindentation," Geochimica et Cosmochimica Acta, vol. 68, No. 20, published in 2004, 7 pages.
International Search Report and Written Opinion issued in International Application No. PCT/US2019/018567 dated Jun. 7, 2019, 19 pages.
Liu et al., "Microstructural and geomechanical analysis of Bakken shale at nanoscale," Journal of Petroleum Science and Engineering, vol. 153, Mar. 23, 2017, 12 pages.
Liu et al., "Applications of nano-indentation methods to estimate nanoscale mechanical properties of shale reservoir rocks," Journal of Natural Gas Science and Engineering, Elsevier, Amsterdam, NL, vol. 35, Sep. 29, 2016, 10 pages.

\* cited by examiner

NANO-INDENTATION TESTS TO CHARACTERIZE HYDRAULIC FRACTURES

TECHNICAL FIELD

This disclosure relates to analyzing rock formations, for example, hydrocarbon-carrying rock formations.

BACKGROUND

Unconventional reservoirs are generally any reservoir (for example, hydrocarbon-carrying reservoir) in which special recovery operations (that is, recovery operations outside conventional operating practices) are employed. Unconventional reservoirs include reservoirs such as tight-gas sands, gas and oil shales, coalbed methane, heavy oil and tar sands, and gas-hydrate deposits, to name a few.

Shale reservoirs, for example, require large hydraulic fracture multistage design in order to maximize barrel of oil equivalent (BOE) well production. Methods to predict the propagation length, height, location and extent of these networks and their connectivities with both inherent natural fractures as well as induced micro- and nano-cracks are important components of reservoir storativity potentials and productivity predictions. Microseismic mapping is used to determine the location and geometry of the hydraulically fractured reservoir with its fracture network and connectivity. The fracture network represented by the microseismic event cloud is then approximated volumetrically in order to better correlate the network to the well performance. This so-called stimulated reservoir volume (SRV), or 3D volume of the created fracture network, is obtained from mapping of microseismic data and then related to the total volume of injected fluid and the well performance.

SUMMARY

This disclosure describes technologies relating to nano-indentation tests to characterize hydraulic fractures.

Certain aspects of the subject matter described here can be implemented, in a first example implementation, as a method. A rock sample is nano-indented from a surface of the rock sample to a specified depth within the rock sample. The specified depth is less than a thickness of the rock sample. The rock sample has physical properties. While nano-indenting the rock sample, multiple depths from the surface to the specified depth and multiple loads applied to the sample are measured. Each load is associated with a respective depth. From the multiple loads and the multiple depths, a change in load over a specified depth is determined. From the change in load over a specified depth, an energy associated with nano-indenting rock sample is determined. From a Scanning Electron Microscope (SEM) image of the nano-indented rock sample, an indentation volume is determined responsive to nano-indenting the rock sample. An energy density associated with the rock sample is determined based, in part, on the determined energy and the indentation volume. It is determined that the energy density associated with the rock sample is substantially equal to energy density of a portion of a subterranean zone in a hydrocarbon reservoir. The subterranean zone is substantially larger than the rock sample. The physical properties of the rock sample are assigned to the portion of the subterranean zone in response to determining that the energy density associated with the rock sample is substantially equal to the energy density of the portion of the subterranean zone.

In an aspect combinable with the first example implementation, the thickness of the rock sample is substantially 1 millimeter. To nano-indent the rock sample, a nano-indenter can be positioned on the surface of the rock sample. The surface of the rock sample can be penetrated using the nano-indenter by a distance that is at least equal to 10 nanometers and less than a thickness of the rock sample.

In another aspect combinable with any of the other aspects, to measure the multiple depths and the multiple loads, the surface of the rock sample can be penetrated using the nano-indenter to a first of the multiple depths. While doing so, a load applied by the nano-indenter on the rock sample from the surface to the first depth can be measured.

In another aspect combinable with any of the other aspects, a distal end of the nano-indenter can have a pyramid shape terminating at a penetrating dip. To determine, from the SEM image of the nano-indented rock sample, and indentation volume, a cross-sectional area of a region penetrated by the nano-indenter can be determined. The indentation volume can be determined based on the cross-sectional area and the specified depth.

In another aspect combinable with any of the other aspects, a plot of the multiple loads versus the multiple depths can be generated. Multiple slopes of the generated plot can be determined. The multiple slopes correspond to multiple changes of load over specified depth including the determined change of load over specified depth.

In another aspect combinable with any of the other aspects, each slope of the multiple slopes represents a failure of the rock sample responsive to the nano-indenting. A failure type can be associated to the determined change of load over specified depth.

In another aspect combinable with any of the other aspects, an area of a portion of the plot that corresponds to the change in load over at the specified depth is determined to determine the energy associated with nano-indenting the rock sample from the change in load over the specified depth.

In another aspect combinable with any of the other aspects, the change in the load can be multiplied by the specified depth to determine the energy associated with nano-indenting the rock sample from the change in load over the specified depth.

In another aspect combinable with any of the other aspects, the energy can be divided by the indentation volume to determine the energy density associated with the rock sample based, in part, on the determined energy and the indentation volume.

Certain aspects of the subject matter described here can be implemented, in a second example implementation, as a method. Energy density of a portion of a subterranean zone in a hydrocarbon reservoir is obtained. An energy density of a rock sample that is substantially smaller than the portion of the subterranean zone is determined. To do so, the rock sample is nano-indented to a depth of less than a thickness of the sample. An energy associated with a pop-in case determined. The pop-in represents a rate of change of nano-indentation loads over a unit depth that is different from a threshold rate of change of nano-indentation loads over the unit depth. An indentation volume is determined responsive to nano-indenting the rock sample. It is determined that the energy density of the portion of the subterranean zone is substantially equal to the determined energy density of the rock sample. Physical properties of the rock sample are assigned to the portion of the subterranean zone in response to determining that the energy density of the portion of the subterranean zone is substantially equal to the determined energy density of the rock sample.

In another aspect combinable with the second implementation, the thickness of the rock sample is between seven and ten times the depth to which the rock sample list nano-indented.

In another aspect combinable with any of the other aspects, the energy density of the portion of the subterranean zone is a first energy density of the first portion of the subterranean zone. The rock sample is a first rock sample. The energy density is a first energy density. Multiple energy densities including the first energy density of multiple portions including the first portion of the subterranean zone are obtained. Multiple energy densities including the first rock density of multiple rock samples including the first rock sample are determined. Physical properties of each rock sample are assigned to a portion of the multiple portions based on a result of combating the multiple energy densities of the multiple portions with the multiple energy densities of the multiple rock samples.

Certain aspects of the subject matter described here can be implemented, in a third example implementation, as a method. Multiple nano-indentation experiments are performed on multiple rock samples. Each nano-indentation experiment includes nano-indenting a rock sample from a surface of the rock sample to a specified depth within the rock sample. The specified depth is less than a thickness of the rock sample. Responsive to the multiple nano-indentation experiments, multiple load-depth curves are obtained. Each load-depth curve identifies, for each rock sample, multiple loads on the rock sample measured during penetration from the surface to the specified depth. From the multiple load-depth curves, multiple pop-ins experienced by the multiple rock samples are determined. Each pop-in is associated with respect to sample. Each pop-in represents a rate of change of loads over a unit depth that this different from a threshold rate of change of loads over the unit depth. Multiple energies associated with the multiple pop-ins are determined. Each energy is released in response to a corresponding pop-in in that aspect of sample. For the multiple rock samples, a corresponding multiple nano-indentation volumes are determined. Each nano-indentation volume represents a volume of the rock sample indented responsive to a corresponding nano-indentation experiment. Multiple energy densities are determined for the multiple rock samples, from the multiple energies, and the multiple nano-indentation volumes. Physical properties of one or more of the rock samples are assigned to one or more portions of a subterranean zone based on a result of combating the multiple energy densities for the multiple rock samples with multiple energy densities of corresponding multiple portions of the subterranean zone.

In another aspect combinable with the third example implementation, each energy of the multiple energies is classified as belonging to one of three categories of energies to determine to multiple energies associated with the multiple pop-ins.

In another aspect combinable with any of the previous aspects, the thickness of each rock sample can be between seven and ten times the depth to which the rock sample is nano-indented.

The details of one or more implementations of the subject matter described in this specification are set forth in the accompanying drawings and the description that follows. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

Figure 1A:
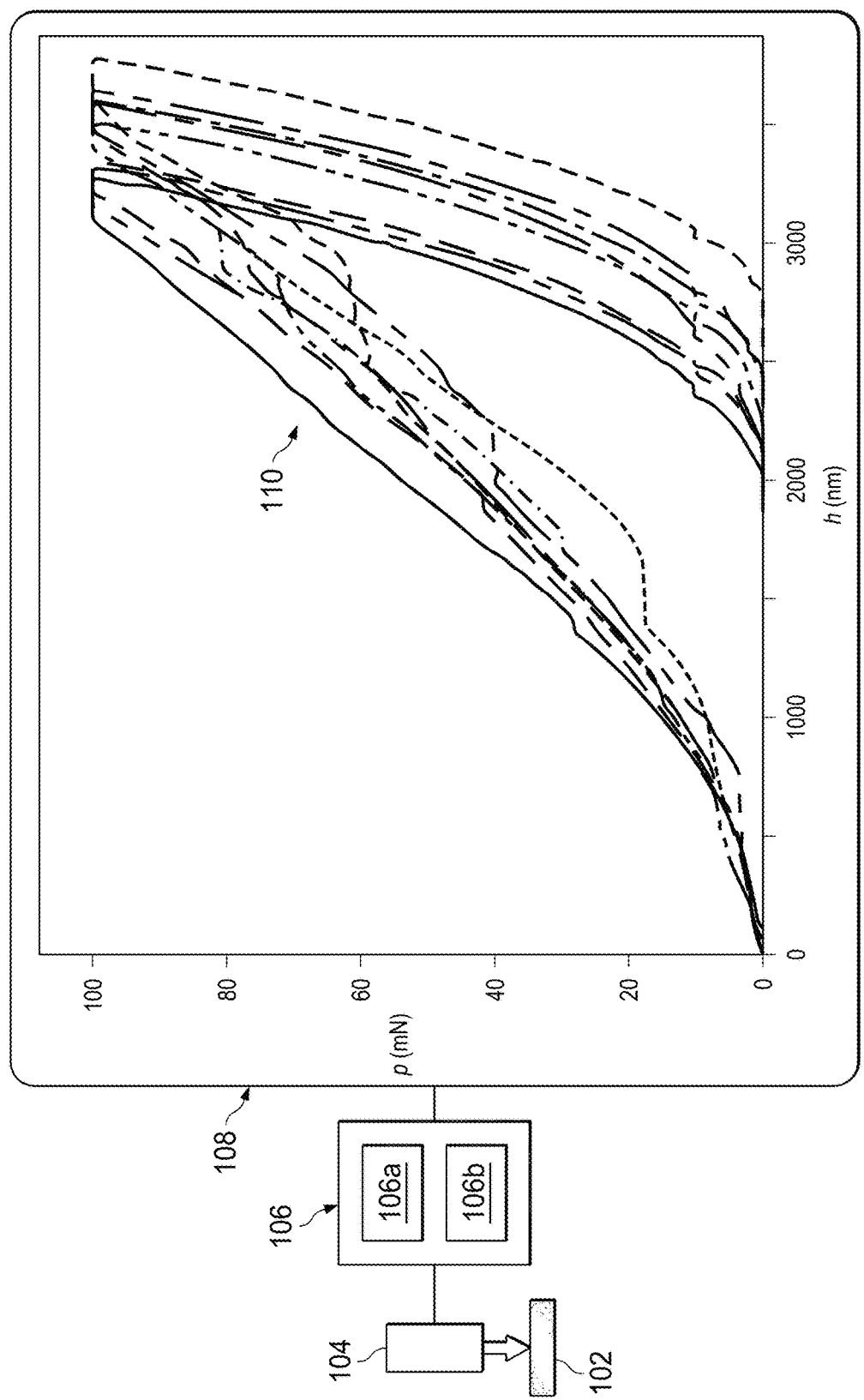
FIGS. 1A-1C are schematic diagrams of performing nano-indenting experiments on rock samples.

Fracture mapping via micro-seismic activity can be unreliable. This disclosure describes techniques to determine the types of shale or rock mechanical failures associated with specific nano- and micro-seismic events. Implementations of the techniques described here can enable a better understanding of the failures associated with sonic recordings and, in turn, enable a better description of the location and geometry of the associated rock or shale micro-fractures compared to existing techniques to do the same. As described in more detail later, the techniques involve identifying pop-ins in nano-indentation load-displacement curves obtained by performing nano-indentation experiments (or tests or operations) on multiple rock samples, for example, shale or other rock sample obtained from unconventional reservoirs.

Pop-ins are localized failures observed in nano-indentation load-displacement curves where a sudden burst of relatively large displacement occurs at a relatively constant force value. In source shales, a multi-phase natural porous material with polymeric organic components, the occurrence of pop-ins has a basis in micromechanics and the failure of granular cohesive-frictional material. Analysis of pop-ins in shale by high resolution scanning electron microscopy (SEM) images has shown that each pop-in or the consecutive series of pop-ins are the result of local brittle or abrupt failure of individual components, such as a silicate grain crushed under a nano-indenter tip or instantaneous planes of slippage between grains, or localized shear failures. In addition, the shear band deformations in a single loading streak form brittle-ductile couplets, thus creating a small burst of energy, (for example, nano-Joules (nJ) of energy), at constant loads also called pop-ins, or, in energy terms, as "sudden energy burst intensity" (SEBI). The tremendous forces exerted by the nano-indenter at these nano- and micro-volume scales trigger local rock failures similar in nature and failure mechanics to tectonic forces and hydraulic fracture energy triggered in fault generation, hydraulic fracturing, and induced micro- and macro-seismic events.

This disclosure describes correlating nano or micro-energy dissipation associated with indentations with microscale volume imprints to discrete shale failure events that could be identical to field macro-scale events registered sonically. Each failure type (for example, crack initiation, catastrophic failure, shearing, abrupt shale or faces dislocation, to name a few) is captured as a nano- or micro-seismic event or activity. Each type of event and its intensity range (correlated to failure mechanism) is established and used to fingerprint the location of the failure, its type, and its associated energy. The information is assimilated for identifying the hydraulic fracturing network extension related to the micro-seismic events relevant to hydraulic fracture propagation azimuth and dimensions associated with the SRV concept.

In this manner, the techniques provide improved characterization of the hydraulic fracturing extension and dimensions created during stimulation. The technique utilizes not only the energy and location of micro-seismic events to determine potential hydraulic fracture extension and dimensions, but also incorporates the type and extent of failure associated with such events. The technique correlates geomechanical interpretations of reservoir source shale failures with geophysical data vis-à-vis energy density at failure, that is, SEBI. The technique is a cost-effective technique for improving estimated SRV models that utilizes existing laboratory resources and micro-seismic data by characterizing the micro-failures correlated to energy density in equivalent volume of shale or rock that has failed.

Figure 1B:
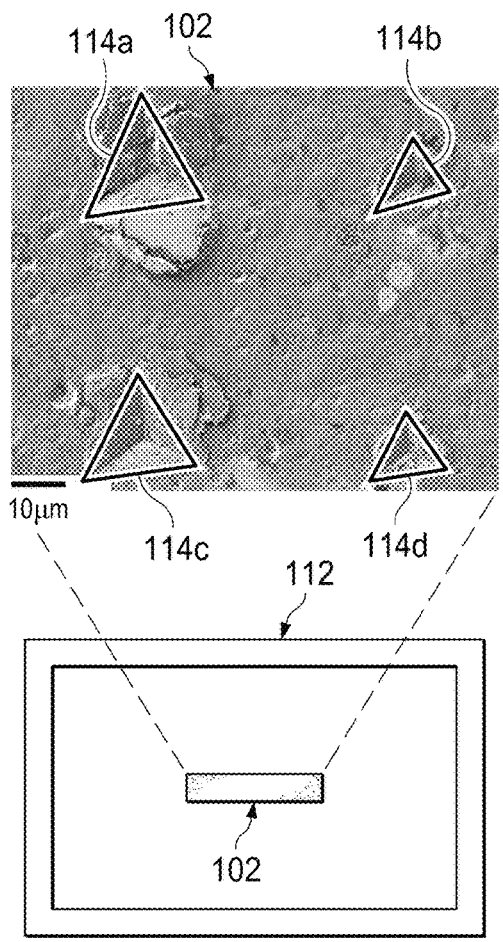
Figure 1C:
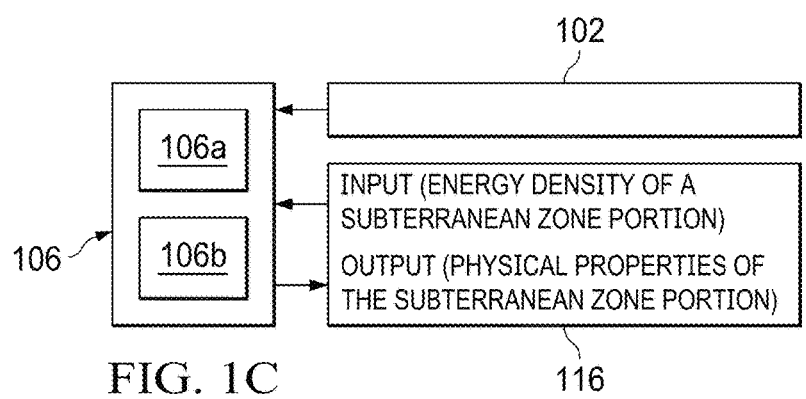

FIGS. 1A-1C are schematic diagrams of performing nano-indenting experiments on rock samples. FIG. 1A is a schematic diagram of a nano-indentation experimentation system (for example, a NanoTest Vantage System™ offered by Micro Materials Limited, Wrexham, UK) performed on a rock sample 102. Example techniques implemented using the system schematically shown in FIGS. 1A-1C are described later.

In some implementations, the rock sample 102 can be a micro-scale rock sample having a thickness in the micrometer range (that is, less than or equal to 1 cm). The upper limit for thickness allows correlating the depth of the test with sample properties being tested at the depth. The rock sample 102 can be obtained from an unconventional reservoir in which hydrocarbons (for example, oil, gas, combinations of them) are entrapped. For example, the rock sample 102 can be a shale sample obtained from a shale reservoir. The rock sample 102 can have certain physical properties, for example, hardness, fracture toughness, elastic moduli, to name a few.

The rock sample 102 can be positioned adjacent to a nano-indenter 104 to nano-indent the sample. For example, the nano-indenter 104 can be a Berkovich indenter with a tip contact area that has been calibrated by indenting into fused silica. Alternatively, the indenter can have a spherical, cono-spherical, cube corner or other geometry.

The system includes a computer system 106 that is operably connected to the nano-indenter 104 and configured to control the nano-indenter 104 to perform operations, for example, nano-indenting the rock sample 102. In some implementations, the computer system 106 can include a computer-readable medium 106a storing computer instructions executable by one or more processors 106a to perform operations including, for example, transmitting instructions to the nano-indenter 104 to perform nano-indenting operations on the rock sample 102 and to receive signals representing results of the nano-indenting operations. The computer system 106 can be connected to input devices (not shown) using which a user can provide instructions, and output devices (for example, a display device 108) on which the computer system 106 can display results of the nano-indenting operations.

For example, the computer system 106 can measure load-displacement curves (for example, the curve 110) responsive to the nano-indentation operations and display the curves in the display device 108. A load-displacement curve shows displacement on the X-axis and load on the Y-axis. The displacement is a depth by which the nano-indenter 104 indents the surface of the rock sample 102. The load is the corresponding load on the nano-indenter 104 to indent to that depth. In general, the depth to which the nano-indenter 104 indents is between seven and ten times the thickness of the rock sample. As described later, pop-ins can be observed in the load-displacement curves.

In FIG. 1A, the computer system 106 is schematically shown to be separate from the nano-indenter 104. In such implementations, the computer system 106 can be a desktop computer, a laptop computer, a tablet computer, a smartphone or other computer system. In some implementations, the nano-indenter 104 and the computer system 106 can be included in the same physical structure. Such a physical structure can also include the display device 110.

FIG. 1B is a schematic diagram of an imaging system 112 to image nano-indentations on the rock sample 102. In some implementations, the imaging system 112 can include a Scanning Electron Microscope (SEM). Alternatively, or in addition, the imaging system 112 can include an Atomic Force Microscope (AFM) or an optical microscope. In general, the imaging system 112 can obtain images at sufficient resolution to be able to see individual indentations and the residual impression left in the rock sample 102. For example, FIG. 1B shows the rock sample 102 having four nano-indentations (nano-indentations 114a, 114b, 114c and 114d). Each nano-indentation is made by the same nano-indenter. The difference in the sizes and shapes of the nano-indentations is due to the difference in the depths to which the nano-indenter 104 penetrated the surface of the rock sample 102. In some implementations, the rock sample 102 can be positioned within the imaging system 112 after nano-indentation by the nano-indenter 104. Alternatively, the nano-indenter 104 can be positioned within the imaging system 112 such that not only the indentations and residual impression but the nano-indentation experiments themselves can also be imaged using the imaging system 112.

FIG. 1C is a schematic diagram of the computer system 106. The computer system 106 can receive, as input, the nano-indentation images captured by the imaging system 112. The computer system 106 can additionally receive, as input, energy density of a portion of a subterranean zone. The subterranean zone can be a formation, a portion of a formation or multiple formations. The physical properties of the reservoir rock can vary across a depth of the subterranean zone from a surface of the Earth. Energy densities at different depths in the subterranean zone can be measured and provided to the computer system 106 as input. For example, the energy densities can be stored on a computer storage medium 116. Based on the nano-indentation images received from the imaging system 112, the computer system 106 can determine an energy density for the rock sample 102. The computer system 106 can compare the energy density for the rock sample 102 with the energy densities of the different portions of the subterranean zone. Based on results of the comparison, the computer system 106 can identify a portion of the subterranean zone whose energy density matches that of the rock sample 102. In response, the computer system 106 can assign physical properties of the rock sample 102 to the rock in the portion of the subterranean zone. For example, the computer system 106 can output the physical properties which can be stored on the computer storage medium 116. By doing so, the computer system 106 can predictively determine physical properties of the subterranean zone using energy densities of rock samples determined from nano-indentation tests.

Figure 2:
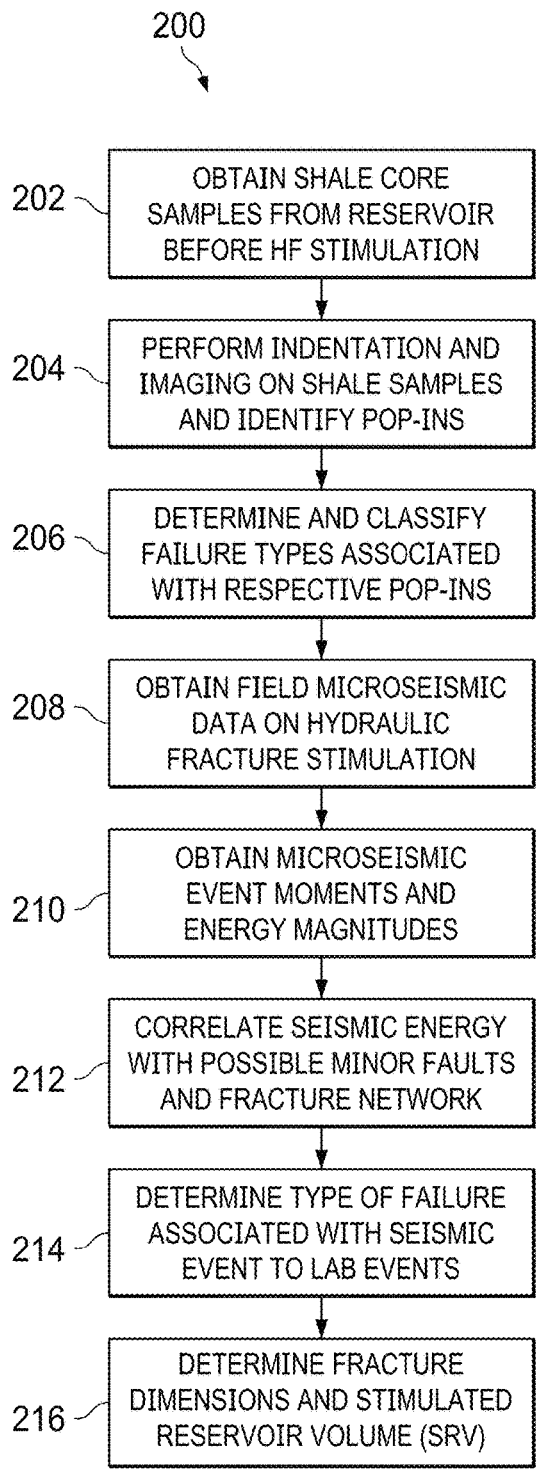
FIG. 2 is a flowchart of an example process to determine fracture dimensions and stimulated reservoir volumes based on the nano-indenting experiments on rock samples.
Figure 3A:
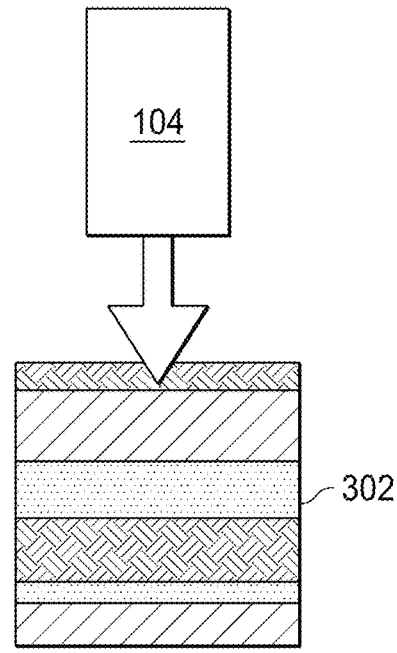
FIGS. 3A and 3B are schematic diagrams of nano-indenting rock samples in directions perpendicular and parallel to the bedding planes.
Figure 3B:
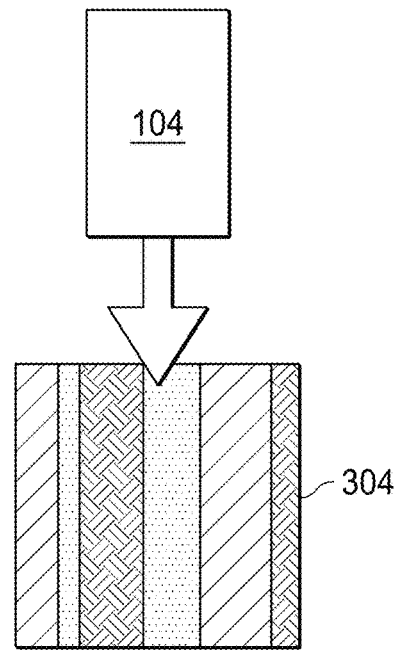

FIG. 2 is a flowchart of an example process 200 to determine fracture dimensions and stimulated reservoir volumes based on the nano-indenting experiments on rock samples. The process 200 can be implemented by the system schematically identified in and described with reference to FIGS. 1A-1C. At 202, core samples are obtained from a subterranean zone (for example, a reservoir such as an unconventional hydrocarbon reservoir). The core samples (for example, shale core samples) can be obtained from the reservoir before hydraulic fracture stimulation. In some implementations, one or more rock samples (for example, like the rock sample 102) can be prepared from the core samples. To do so, each core sample can be mechanically cut and polished to create rock samples, each having a substantially flat indentation surface and a thickness of substantially 1 millimeter (mm). In general, a rock sample can be cut and polished to a thickness that can allow performing as much as several hundred nano-indentations without traversing the thickness of the sample. FIGS. 3A and 3B are schematic diagrams of nano-indenting rock samples in directions perpendicular and parallel to the bedding planes. One or more of the rock samples (for example, rock sample 304 in FIG. 3A) can be cut and polished such that the indentation surface is parallel to the bedding plane of the sample and nano-indentation will be perpendicular to the bedding plane. Other rock samples (for example, rock sample 306 in FIG. 3B) can be cut and polished such that the indentation surface is perpendicular to the bedding plane of the sample and nano-indentation will be parallel to the bedding plane of the sample.

At 204, indentation and imaging can be performed one or more times on each rock sample. For each nano-indentation, the nano-indenter 104 can be penetrated from the indentation surface of the rock sample to a specified depth within the sample. The specified depth is less than a thickness of the sample. While nano-indenting the rock sample, the computer system 106 (or both) can measure multiple depths from the surface to the specified depth and multiple loads applied to the sample. Each load is associated with a respective depth. From the measured depths and loads, the computer system 106 (or both) can develop load-displacement curves for each nano-indentation. For example, one or more (or all) of nano-indentation experiments can involve applying loads ranging from 1 milli Newton (mN) to 400 mN to depths ranging from 100 nanometer (nm) to 7,000 nm.

A subset of (that is, one or more or all of) the rock samples may exhibit pop-ins, which are characterized by a sudden increase in displacement with or without a necessary change in force on the load-displacement curve. Pop-ins can appear immediately and frequently throughout source shale nano-indentation testing. In many cases, the first burst is not unique in a single load-displacement curve cycle but rather is followed by additional sudden bursts. For example, pop-ins can be seen in the load displacement curve 108 (FIG. 1A) was developed from test data containing two sets of 10 indentations performed on shale samples at a maximum load of 100 mN. A pop-in can be characterized by catastrophic failures such as grain crushing, grain pile-ups, multilayer pile-ups and grain punching into softer layers. In some instances, a rock sample may not exhibit any pop-in. Such samples are ignored in the analysis described in this disclosure.

Figure 4A:
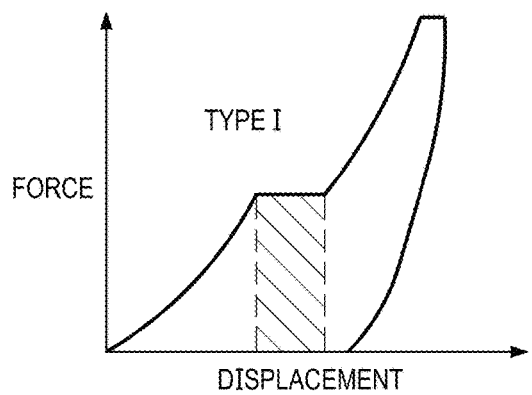
FIGS. 4A-4C are schematic diagrams of three different types of pop-ins.
Figure 4B:
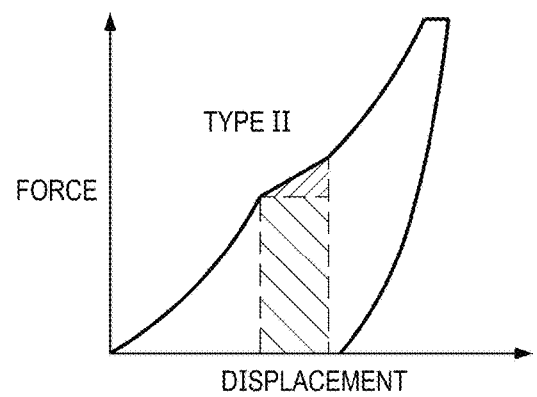
Figure 4C:
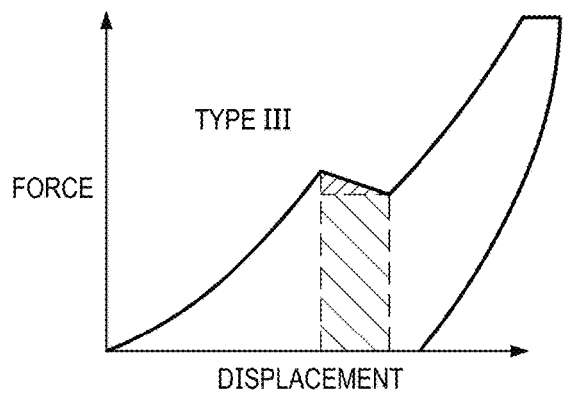

At 206, failure types associated with respective pop-ins can be determined and classified. For each load-displacement curve, the computer system 106 can be configured to determine a change in load (p) over a specified depth (h) to identify a slope, that is, a gradient of force over displacement ($\Delta p/\Delta h$), from which pop-ins can be observed or determined. FIGS. 4A-4C are schematic diagrams of three different types of pop-ins, each corresponding to a different failure mechanism. FIG. 4A shows a Type I pop-in in which the load-displacement curve exhibits a discontinuity at a constant force. Thus, the gradient of force over displacement, that is, $\Delta p/\Delta h$, is zero. A Type I pop-in falls between two nearly elastic responses on the load-displacement curve when the nano-indentation direction is perpendicular to the bedding plane (sample 302, FIG. 3A). That is, after the Type I pop-in, a linear elastic deformation took place before the onset of a Type II pop-in. FIG. 4B shows a Type II pop-in defined by a sudden displacement in the load-displacement curve where the slope ($\Delta p/\Delta h$) is greater than zero. FIG. 4C shows a Type III pop-in defined by a sudden displacement in the load-displacement curve where the slope ($\Delta p/\Delta h$) is less than zero.

To determine pop-ins, the computer system 106 can store loads and corresponding displacements for each nano-indentation experiment in a computer-readable medium (for example, the computer-readable medium 106b or separate computer storage medium). To determine a change in load, the computer system 106 can determine a difference of a stored load value and a stored preceding load value. The two values can be consecutive (that is, with no intermediate load values) or can be successive (that is, with intermediate load values). Similarly, to determine a change in displacement, the computer system 106 can determine a difference of a stored displacement value and a stored preceding displacement value, which can be consecutive or successive. To determine a pop-in, the computer system 106 can determine a slope by dividing the change in load by the change in slope. The computer system 106 can determine if the slope is zero, greater than zero or less than zero, and, based on the result, classify a pop-in as Type I, Type II or Type III, respectively. In sum, for each load-displacement curve in a nano-indentation experiment, the computer system 106 can store the number of pop-ins and the type of each pop-in. In alternative or additional implementations, pop-ins can be observed and determined manually using the load-displacement curves.

A single load-displacement curve measurement can yield multiple pop-ins. For example, as described earlier, multiple pop-ins can be seen in the load displacement curve 108 (FIG. 1A) was developed from test data containing two sets of 10 indentations performed on shale samples at a maximum load of 100 mN. Moreover, multiple load-displacement curves can be generated for the same rock sample. Depending on the area of the indentation surface, multiple nano-indentation experiments can be performed at multiple, different locations on the rock sample. For example, FIG. 1B shows four nano-indentation experiments performed on the rock sample 102. In addition, multiple rock samples can be formed from the same core sample and subjected to the nano-indentation experiments. Thus, the computer system 106 can identify multiple pop-ins for rock obtained from a particular portion of the subterranean zone.

As described earlier, in source shales, a multi-phase natural porous material with polymeric organic components, the occurrence of pop-ins has a basis in micromechanics and the failure of granular cohesive-frictional material. In other words, a pop-in is representative of physical properties of the rock sample. The physical properties of the rock obtained from the particular portion of the subterranean zone can be determined using known techniques. In addition, the nano-indentation techniques described here can be used to determine the physical properties of individual rock samples. The computer system 106 can correlate pop-ins observed or determined for rock obtained from a particular portion of the subterranean zone to the physical properties of the rock obtained from that portion of the subterranean zone. As described later, the computer system 106 can develop the correlation using energy densities associated with the rock.

As described earlier, an imaging system 112 (for example, a SEM or AFM) can be used to image the nano-indentations and to provide the images to the computer system 106. The computer system 106 can determine energy densities for a rock sample using the images and using the one or more load-displacement curves measured for that sample. Energy density, in this context, refers to the energy required, for example, to fracture the rock during nano-indentation of the rock sample. Energy density also refers, on a comparatively larger scale, to microseismic energy densities detected in observation wells by geosensors or acoustic sensors. To determine the energy for Type I pop-ins, the load at which the pop-in occurs is multiplied by the total displacement of the indenter over the span of the pop-in (that is, the final depth–the initial depth). To determine the energy for Type II pop-ins, the average load at which the pop-in occurs (that is, (final load–initial load)/2) is multiplied by the total displacement of the indenter over the span of the pop-in (that is, final depth–initial depth). Approximately 70% of the pop-in events dissipated less than 7 nano Joules (nJ) of energy while less than 5% of the pop-ins produced more than 40 nJ of energy. Pop-ins occur across a wide range of depths or loads or both.

Energy density, then, is the energy to fracture the rock per unit volume of the rock. In some implementations, energy density of a rock sample is determined by dividing the energy to fracture the rock sample by the volume of indented rock sample. In some implementations, the volume of the indented rock sample can be determined by measuring the residual shape left by the nano-indenter on the surface of the rock sample using the imaging system 112, and performing geometric calculations. For example, if the tip of the nano-indenter 104 is shaped like a pyramid, then the residual shape left by the nano-indenter on the surface of the rock sample can be approximated to be rectangular. Tips of other nano-indenters with other shapes can leave correspondingly different residual shapes on the rock sample surface. The volume of the indented rock sample can then be determined by multiplying the residual shape by the depth of indentation. In some implementations, the computer system 106 can be configured to implement image analysis techniques to determine the dimensions of the residual shape, determine an area of the residual shape from the dimensions and multiply the area by the nano-indentation depth that is, for example, stored in the computer-readable medium. Alternatively, the dimensions or the area or the volume (or any combination of them) can be manually calculated, for example, by a user, and provided to the computer system 106 as an input. The computer system 106 can be configured to determine the energy density for the rock sample by implementing the techniques described earlier.

At 208, field micro-seismic data are obtained on hydraulic fracture propagation. For example, the micro-seismic data are obtained via geophones by receiving an acoustic wave signal transmitted by localized fractures shearing (thus sending an acoustic signal) due to the propagation of the main hydraulic fracture in the subterranean zone. The volume of the hydraulically fractured subterranean zone, can be determined from the decibel levels of individual microseismic signals collected as the HF propagates. For example, the acoustic wave can be transmitted through a fracture that is about 100 feet high and about 1,000 feet long, and the response can be evaluated to determine the energy density.

At 210, micro-seismic event moments and energy magnitudes are obtained. Microseismic monitoring typically results in capturing the location of events and the magnitude or strength (or both) of the events. Moment magnitude is used to describe a microseismic event. Moment magnitude relates to the distance the rock moves along a fault or fracture and the area of the fault or surface of the fracture. The moment magnitude is the amount of energy released by the event.

At 212, seismic energy obtained from the field (by implementing step 210) is correlated with energy density determined from the nano-indentation experiments. To do so, for example, the computer system 106 can match field-level energy density values for a portion of a subterranean zone to energy density values determined for the rock samples.

At 214, a type of failure associated with the seismic events can be determined. For example, upon determining that an energy density value determined for a rock sample matches a field-level energy density value for a portion of the subterranean zone, the computer system 106 can associate pop-ins determined for the rock sample to the portion of the subterranean zone. The association is a prediction that rock in the portion of the subterranean zone will exhibit the same or substantially identical types of failures as that exhibited by the rock sample. Accordingly, the computer system 106 can assign the physical properties determined for the rock sample to the portion of the subterranean zone. In this manner, the physical properties of the portion of the subterranean zone can be predictively determined.

At 216, fracture dimensions and SRV can be determined. The stimulated reservoir volume (SRV) is an estimate of the volume of the open fractures which are contributing to the flow of hydrocarbons to the well. The microseismic data which includes the location and magnitude of failure events provides an overall picture of the fractured formation.

Figure 5:
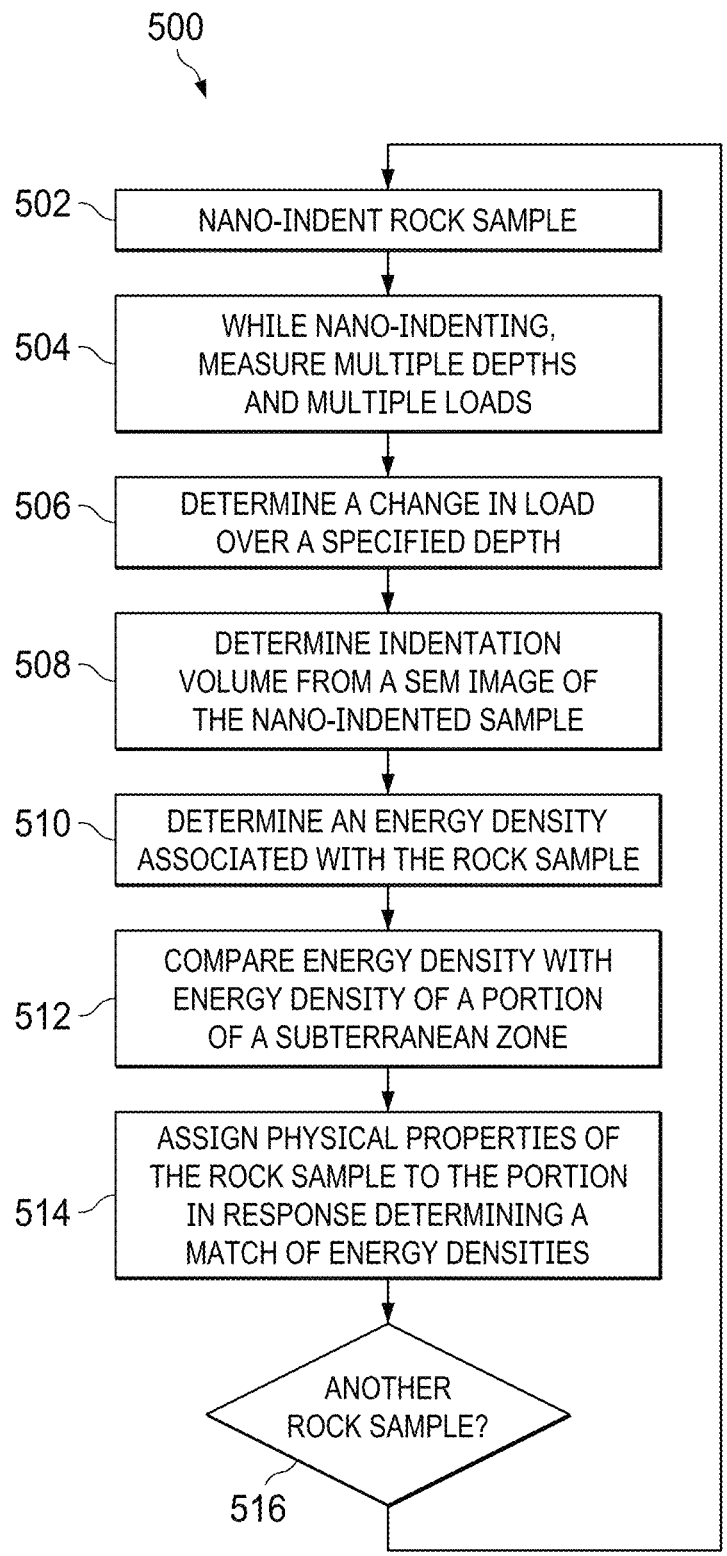
FIG. 5 is a flowchart of an example process of determining physical properties of a subterranean zone based on nano-indenting experiments on rock samples.

FIG. 5 is a flowchart of an example process 500 of determining physical properties of a subterranean zone based on nano-indenting experiments on rock samples. The process 500 can be implemented either entirely or in part using the system described with reference to FIGS. 1A-1C. At 502, a rock sample is nano-indented from a surface of the rock sample to a specified depth within the rock sample. At 504, while nano-indenting the rock sample, multiple depths from the surface to the specified depth and multiple loads applied to the sample are measured, each load associated with a respective depth. At 506, a change in load over a specified depth is determined from the multiple loads and multiple depths. At 508, an indentation volume is determined from an image (for example, a SEM image or an AFM image) of the nano-indented sample. At 510, an energy density associated with the rock sample is determined based, in part, on the determined energy and the indentation volume. At 512, the energy density is compared with energy density of a portion of a subterranean zone. It is determined that the energy density associated with the rock sample is substantially equal to energy density of a portion of a subterranean zone in a hydrocarbon reservoir. The subterranean zone is substantially larger than the rock sample. At 514, the physical properties of the rock sample are assigned to the portion of the subterranean zone in response to determining that the energy density associated with the rock sample is substantially equal to energy density of a portion of a subterranean zone in a hydrocarbon reservoir. At 516, it is determined if another rock sample is available to be nano-indented. Alternatively or in addition, it can be determined if the same rock sample is to be further nano-indented. If yes, then the process 500 is repeated starting at step 502. If no, then the process 500 ends.

Thus, particular implementations of the subject matter have been described. Other implementations are within the scope of the following claims.

The invention claimed is:

1. A method comprising:
   nano-indenting a rock sample from a surface of the rock sample to a specified depth within the rock sample, the specified depth less than a thickness of the rock sample, the rock sample having physical properties;
   while nano-indenting the rock sample, measuring a plurality of depths from the surface to the specified depth and a plurality of loads applied to the sample, each load associated with a respective depth;
   determining, from the plurality of loads and the plurality of depths, a change in load over a specified depth;
   determining, from the change in load over a specified depth, an energy associated with nano-indenting the rock sample;
   determining, from a Scanning Electron Microscope (SEM) image of the nano-indented rock sample, an indentation volume responsive to nano-indenting the rock sample;
   determining an energy density associated with the rock sample based, in part, on the determined energy and the indentation volume;
   determining that the energy density associated with the rock sample is substantially equal to energy density of a portion of a subterranean zone in a hydrocarbon reservoir, the subterranean zone being substantially larger than the rock sample; and
   assigning the physical properties of the rock sample to the portion of the subterranean zone in response to determining that the energy density associated with the rock sample is substantially equal to the energy density of the portion of the subterranean zone.

2. The method of claim 1, wherein the thickness of the rock sample is substantially 1 millimeter, and wherein nano-indenting the rock sample comprises:
   positioning a nano-indenter on the surface of the rock sample;
   penetrating the surface of the rock sample using the nano-indenter by a distance that is at least equal to 10 nanometers and less than a thickness of the rock sample.

3. The method of claim 2, wherein, while nano-indenting the rock sample, measuring a plurality of depths from the surface to the specified depth and a plurality of loads applied to the sample, each load associated with a respective depth comprises:
   penetrating the surface of the rock sample using the nano-indenter by the distance to a first depth of the plurality of depths; and
   while penetrating the surface of the rock sample to the first depth, measuring a load applied by the nano-indenter on the rock sample from the surface to the first depth.

4. The method of claim 2, wherein a distal end of the nano-indenter has a pyramid shape terminating at a penetrating tip, wherein determining, from the SEM image of the nano-indented rock sample, an indentation volume responsive to nano-indenting the rock sample comprises:
   determining, from the SEM image, a cross-sectional area of a region penetrated by the nano-indenter; and
   determining the indentation volume based on the cross-sectional area and the specified depth.

5. The method of claim 1, further comprising:
   generating a plot of the plurality of loads versus the plurality of depths; and
   determining a plurality of slopes of the generated plot corresponding to a plurality of changes of load over specified depth, the plurality of changes of load over specified depth including the determined change of load over specified depth.

6. The method of claim 5, wherein each slope of the plurality of slopes represents a failure of the rock sample responsive to the nano-indenting, wherein the method further comprises associating a failure type to the determined change of load over specified depth.

7. The method of claim 5, wherein determining, from the change in load over the specified depth, the energy associated with nano-indenting the rock sample comprises determining an area of a portion of the plot that corresponds to the change in load over the specified depth.

8. The method of claim 7, wherein determining, from the change in load over the specified depth, the energy associated with nano-indenting the rock sample comprises multiplying the change in the load by the specified depth.

9. The method of claim 8, wherein determining the energy density associated with the rock sample based, in part, on the determined energy and the indentation volume comprises dividing the energy by the indentation volume.

10. A method comprising:
    obtaining energy density of a portion of a subterranean zone in a hydrocarbon reservoir;
    determining an energy density of a rock sample that is substantially smaller than the portion of the subterranean zone by:
      nano-indenting the rock sample to a depth less than a thickness of the sample;
      determining an energy associated with a pop-in representing a rate of change of nano-indentation loads over a unit depth that is different from a threshold rate of change of nano-indentation loads over the unit depth; and
      determining an indentation volume responsive to nano-indenting the rock sample;
    determining that the energy density of the portion of the subterranean zone is substantially equal to the determined energy density of the rock sample; and
    assigning physical properties of the rock sample to the portion of the subterranean zone in response to determining that the energy density of the portion of the subterranean zone is substantially equal to the determined energy density of the rock sample.

11. The method of claim 10, wherein the thickness of the rock sample is between seven and ten times the depth to which the rock sample is nano-indented.

12. The method of claim 10, wherein the energy density of the portion of the subterranean zone is a first energy density of a first portion of the subterranean zone, wherein the rock sample is a first rock sample, the energy density is a first energy density, and wherein the method further comprises:
    obtaining a plurality of energy densities including the first energy density of a plurality of portions including the first portion of the subterranean zone;
    determining a plurality of energy densities including the first rock density of a plurality of rock samples including the first rock sample; and assigning physical properties of each rock sample to a portion of the plurality of portions based on a result of comparing the plurality of energy densities of the plurality of portions with the plurality of energy densities of the plurality of rock samples.

13. A method comprising:

performing a plurality of nano-indentation experiments on a plurality of rock samples, each nano-indentation experiment comprising nano-indenting a rock sample from a surface of the rock sample to a specified depth within the rock sample, the specified depth less than a thickness of the rock sample;

obtaining, responsive to the plurality of nano-indentation experiments, a plurality of load-depth curves, each load-depth curve identifying, for each rock sample, a plurality of loads on the rock sample measured during penetration from the surface to the specified depth;

determining, from the plurality of load-depth curves, a plurality of pop-ins experienced by the plurality of rock samples, each pop-in associated with a respective sample, each pop-in representing a rate of change of loads over a unit depth that is different from a threshold rate of change of loads over the unit depth;

determining a plurality of energies associated with the plurality of pop-ins, each energy released in response to a corresponding pop-in in the respective sample;

determining, for the plurality of rock samples, a corresponding plurality of nano-indentation volumes, each nano-indentation volume representing a volume of the rock sample indented responsive to a corresponding nano-indentation experiment;

determining a plurality of energy densities for the plurality of rock samples from the plurality of energies and the plurality of nano-indentation volumes; and assigning physical properties of one or more of the rock samples to one or more portions of a subterranean zone based on a result of comparing the plurality of energy densities for the plurality of rock samples with a plurality of energy densities of a corresponding plurality of portions of the subterranean zone.

14. The method of claim 13, wherein determining the plurality of energies associated with the plurality of pop-ins, each energy released in response to a corresponding pop-in in the respective sample comprises:

classifying each energy of the plurality of energies as belonging to one of three categories of energies.

15. The method of claim 13, wherein the thickness of each rock sample is between seven and ten times the depth to which the rock sample is nano-indented.

* * * * *